United States Patent
Yagi

(10) Patent No.: US 10,166,363 B2
(45) Date of Patent: Jan. 1, 2019

(54) CATHETER

(71) Applicant: ASAHI INTECC CO., LTD., Nagoya-shi, Aichi (JP)

(72) Inventor: Takayuki Yagi, Seto (JP)

(73) Assignee: ASAHI INTECC CO., LTD., Nagoya-shi (JP)

( * ) Notice: Subject to any disclaimer, the term of this patent is extended or adjusted under 35 U.S.C. 154(b) by 441 days.

(21) Appl. No.: 14/694,426

(22) Filed: Apr. 23, 2015

(65) Prior Publication Data

US 2015/0306347 A1  Oct. 29, 2015

(30) Foreign Application Priority Data

Apr. 25, 2014 (JP) ................................ 2014-090784

(51) Int. Cl.
*A61M 25/00* (2006.01)
*A61M 25/01* (2006.01)
*A61M 25/10* (2013.01)

(52) U.S. Cl.
CPC ...... *A61M 25/0067* (2013.01); *A61M 25/005* (2013.01); *A61M 25/008* (2013.01); *A61M 25/0045* (2013.01); *A61M 25/0052* (2013.01); *A61M 25/0138* (2013.01); *A61M 25/0051* (2013.01); *A61M 25/0053* (2013.01);
(Continued)

(58) Field of Classification Search
CPC .. A61M 2025/1093; A61M 2025/0046; A61M 2025/0047; A61M 2025/0048; A61M 2025/0081; A61M 25/0045; A61M 25/005; A61M 25/0051; A61M 25/0052; A61M 25/0053; A61M 25/0067; A61M 25/008; A61M 25/0138; A61M 25/0068
See application file for complete search history.

(56) References Cited

U.S. PATENT DOCUMENTS 5,496,294 A * 3/1996 Hergenrother .... A61M 25/0052
604/264
7,815,626 B1 * 10/2010 McFadden ........ A61M 25/0045
600/585
(Continued)

FOREIGN PATENT DOCUMENTS

JP  H08-308933 A  11/1996
JP  2001-190680 A  7/2001
(Continued)

OTHER PUBLICATIONS

Sep. 22, 2015 Extended European Search Report issued in corresponding European Patent Applicatin No. 15161844.4.
(Continued)

*Primary Examiner* — Nathan R Price
*Assistant Examiner* — Anh Bui
(74) *Attorney, Agent, or Firm* — Oliff PLC

(57) ABSTRACT

A catheter includes a catheter shaft having an inner layer, a reinforcing body covering the inner layer, and an outer layer covering the reinforcing body. Additionally, a tubular metallic distal end tip is provided at the distal end of the catheter shaft, and a slit is formed on the distal end tip. An outer peripheral surface of the distal end tip is provided with outer coating such that the outer coating is disposed within the slit. Thus, the metallic distal end tip may bend easily and the distal end tip is not easily caught on, for example, a lesion.

15 Claims, 6 Drawing Sheets

(52) U.S. Cl.
CPC . *A61M 25/0068* (2013.01); *A61M 2025/0046* (2013.01); *A61M 2025/0047* (2013.01); *A61M 2025/0048* (2013.01); *A61M 2025/0081* (2013.01); *A61M 2025/1093* (2013.01)

(56) References Cited

U.S. PATENT DOCUMENTS

| | | |
|---|---|---|
| 2008/0255507 A1 | 10/2008 | Mushtaha |
| 2009/0216185 A1 | 8/2009 | Gregorich et al. |
| 2010/0004631 A1* | 1/2010 | Zhou .................. A61L 29/085 604/527 |
| 2011/0152791 A1* | 6/2011 | Kobayashi ............ A61L 29/085 604/265 |

FOREIGN PATENT DOCUMENTS

| | | |
|---|---|---|
| JP | 2005-230318 A | 9/2005 |
| JP | 2007-244492 A | 9/2007 |
| JP | 2011-512956 A | 4/2011 |
| WO | 2009/108816 A1 | 9/2009 |

OTHER PUBLICATIONS

Mar. 3, 2016 Office Action issued in Japanese Patent Application No. 2014-090784.
Sep. 18, 2017 Office Action issued in Chinese Patent Application No. 201510088648.3.
Feb. 23, 2018 Office Action issued in Chinese Patent Application No. 201510088648.3.
Sep. 14, 2018 Office Action issued in Chinese Patent Application No. 201510088648.3.

\* cited by examiner

CATHETER

CROSS REFERENCE TO RELATED APPLICATION

This application claims priority to Japanese Patent Application No. 2014-090784 filed in the Japan Patent Office on Apr. 25, 2014, the entire contents of which are incorporated herein by reference.

BACKGROUND

The disclosed embodiments relate to a catheter that is capable of, for example, passing by or through a hard lesion. Japanese Unexamined Patent Application Publication No. 2007-244492 discloses a traditional catheter having a metallic distal end with sufficient hardness. Thus, the catheter is inserted into a hard lesion formed inside, for example, a blood vessel, a bile duct, or a pancreatic duct, or the catheter is inserted into bone in order to suck bone marrow. However, the distal end of the catheter of Japanese Unexamined Patent Application Publication No. 2007-244492 does not also have flexibility. U.S. Patent Application Publication No. 2008/0255507 discloses a traditional catheter in which a resin distal end tip is provided with a groove in order to provide flexibility.

SUMMARY

Unevenness is a common problem associated with the traditional catheters that include a groove or slit on a distal end tip. Such unevenness may cause the surface of the distal end tip to be irregular so that the distal end tip may be easily caught on, for example, a lesion. The embodiments of the present disclosure address these deficiencies of the traditional catheters by providing a smooth metallic distal end with a slit that allows the distal end to bend easily. Therefore, due to its smoothness and bendability, the distal end tip is not easily caught on, for example, a lesion. Additionally, the embodiments of the present disclosure provide a catheter that has sufficient flexibility, so that it may pass through, for example, a tortuous blood vessel such as a peripheral vessel, while maintaining hardness, so that it may pass by or through, for example, a hard lesion.

The disclosed embodiments include a catheter that includes a tube body comprising an inner layer, a reinforcing body covering the inner layer, and an outer layer covering the reinforcing body. A metallic distal end tip is provided at a distal end of the tube body, and a slit is formed on the distal end tip. Additionally, an outer peripheral surface of the distal end tip is provided with an outer coating such that the outer coating is disposed within the slit.

In the disclosed embodiments, the metallic distal end tip is provided with the slit, thus allowing the distal end tip to bend easily. Moreover, an outer peripheral surface of the distal end tip is covered with an outer coating, thus providing a smooth outer surface of the distal end tip. The smooth outer surface makes it difficult for the distal end tip to be caught on, for example, a lesion.

The outer coating enters and is thus disposed within the inside of the slit so that the outer coating is firmly fixed to the distal end tip (an anchoring effect), which makes it possible to securely maintain the smooth surface of the distal end tip.

An inner coating may be provided on an inner peripheral surface of the distal end tip so that the outer coating, disposed within the inside of the slit, contacts the inner coating.

In embodiments, the distal end tip is covered with the outer coating and the inner coating, and the outer coating is disposed within the inside of the slit so that the inner coating is in close contact with the outer coating. Thus, the outer coating and the inner coating can be firmly fixed to the distal end tip.

Moreover, the inner coating can also smooth the inner peripheral surface of the distal end tip, which prevents and/or reduces a medical instrument (a guide wire, for example) passing through an inner lumen of the catheter from becoming caught on the inner peripheral surface of the distal end tip.

In embodiments, the outer coating and the outer layer of the tube body may be integrally formed, and the inner coating and the inner layer of the tube body may be integrally formed.

In the catheter of the disclosed embodiments, the outer coating and the outer layer of the tube layer are integrally formed, and the inner coating and the inner layer of the tube body are integrally formed, whereby a connection portion between the distal end tip and the tube body is seamless. Such a seamless connection portion prevents and/or reduces the catheter from being caught on an outside object, for example, on a lesion. The seamless connection portion also prevents and/or reduces a medical instrument (for example, a guide wire) passing through an inner lumen of the catheter from being caught on the catheter. Additionally, the seamless connection portion enhances connection strength between the distal end tip and the tube body.

A coil body formed by winding metallic element wires into a helical coil structure may be used as a reinforcing body, and the distal end tip may be welded to the distal end of the coil body.

The coil body and the distal end tip are joined by welding. Thus, it is possible to further enhance connection strength between the distal end tip and the tube body.

Furthermore, the distal end of the coil body is a reinforcing body that includes a part formed integrally by mutually-melted element wires constituting the coil body, and the distal end tip may be welded to the part.

The element wires are mutually melted and formed integrally at the distal end portion of the coil body to prevent and/or reduce loosening of the element wires from the coil body. As a result, it is possible to easily weld the distal end tip and the distal end portion of the coil body.

DETAILED DESCRIPTION OF EMBODIMENTS

Figure 1:
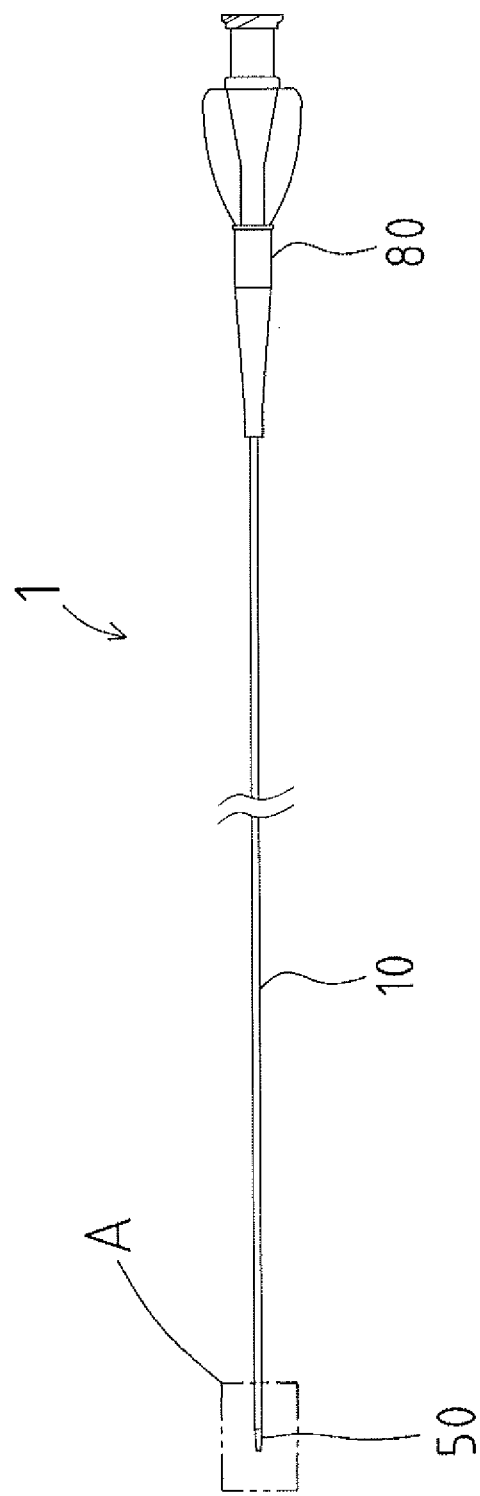
FIG. 1 schematically illustrates a catheter according to embodiments.
Figure 2A:
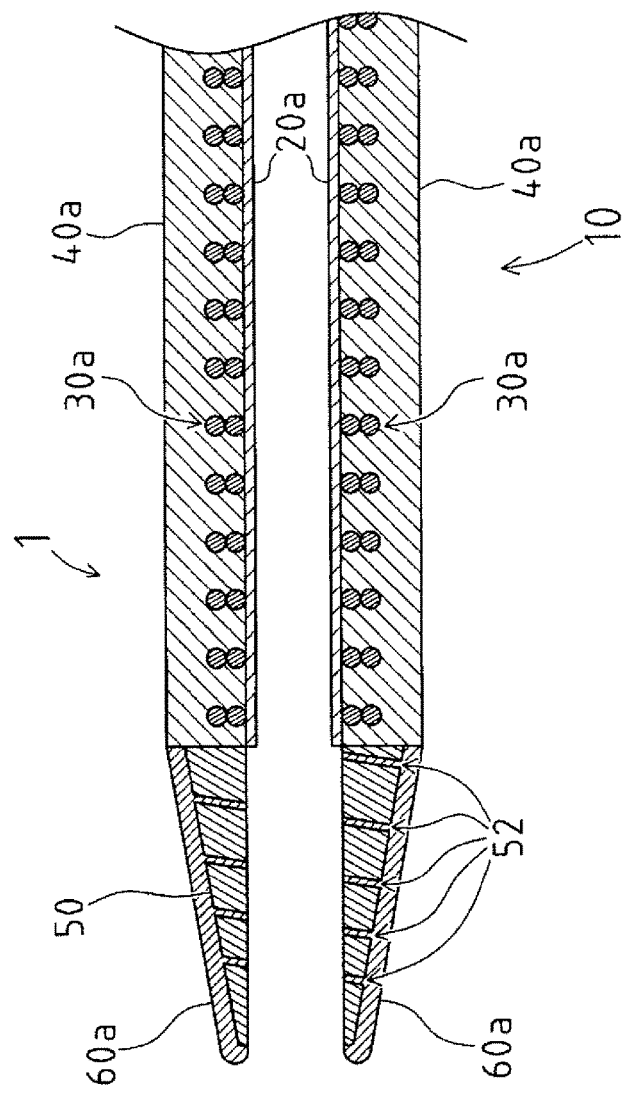
FIG. 2A is a cross-sectional view of part A of the catheter of FIG. 1.

As shown in FIG. 1, catheter 1 includes a catheter shaft 10, a connector 80 that is provided at the proximal end portion of the catheter shaft 10 (tube body), and a distal end tip 50 that is provided at the distal end portion of the catheter shaft 10. In the embodiments, the catheter shaft may correspond to a tube body. FIG. 2A is an enlarged view illustrating the vicinity of a distal end of the catheter 1 (an area A as shown in FIG. 1). The catheter shaft 10 is a tubular structural body that may include an inner layer 20a, a braid layer 30a covering the inner layer 20a, and an outer layer 40a covering the braid layer 30a. In embodiments, the braid layer 30a may form a reinforcing layer.

The inner layer 20a may be formed of a resin material that is known to one of skill in the art. Thus, the specific resin material forming the inner layer 20a is not especially limited. However, polytetrafluoroethylene (PTFE) is preferable in order to provide sufficient slidability with an instrument (for example, with a guide wire or with another catheter) inserted within an inner lumen of catheter 1.

The braid layer 30a may be formed by braiding and/or winding element wires. The material of the element wires is not especially limited, and the materials may include those that are known to one of skill in the art. For example, the material of the element wires may include stainless steel (SUS304, SUS316, etc.), gold, white gold, tungsten, platinum, nickel, an alloy of such elements, or a mixture of these materials.

The outer layer 40a may be formed of a resin material that is known to one of skill in the art. Thus, the specific resin material forming the outer layer 40a is not especially limited, and may include, for example, polyamide, polyamide elastomer, polyester, and polyurethane.

The metallic distal end tip 50 is provided at the distal end portion of the catheter shaft 10. The distal end tip 50 may include an outer diameter that is tapered so that its diameter decreases toward the distal end. Such a tapered distal end tip 50 may allow the catheter 1 to have sufficient passing performance relative to a hard lesion (e.g., a calcified lesion).

The metallic material used for the distal end tip 50 is not especially limited, and may include, for example, stainless steel (SUS304, SUS316, etc.), gold, white gold, tungsten, platinum, nickel, an alloy of such elements, or a mixture of these materials. The distal end tip 50 is preferably formed of a radiopaque metallic material so that a position of the distal end of the catheter 1 may be viewed as a radioscopic image.

Figure 2B:
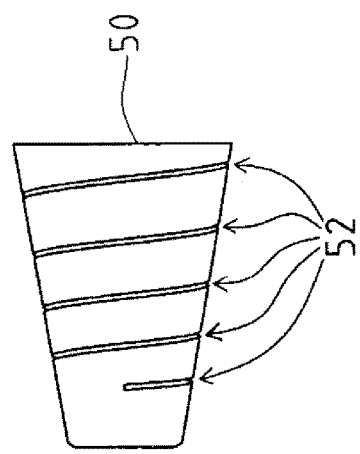
FIG. 2B is an external view of the metallic distal end tip used in part A of the catheter of FIG. 1.

Moreover, the distal end tip 50 is provided with a slit 52, as shown in FIGS. 2A and 2B. The slit 52 may lighten the metallic distal end tip 50 and thus improve the flexibility thereof.

The slit 52 may be formed helically on the distal end tip 50, which may allow the distal end tip 50 to be bent in any direction with the same level of easiness. Alternatively, the slit 52 may include various shapes and patterns. Moreover, the pitch of the slit 52 may be smaller toward the distal end so that the distal end area of the distal end tip 50 is especially flexible. Thus, the distal end tip 50 may be sufficiently flexible so as to reduce the risk of perforating a blood vessel by the distal end tip 50.

Furthermore, as illustrated in FIG. 2A, the outer peripheral surface of the distal end tip 50 may be covered with an outer coating 60a. The outer coating 60a may be disposed within the slit 52 on the distal end tip 50.

The slit 52 may allow the distal end tip 50 to bend easily, while the hardness thereof is maintained. Moreover, the outer peripheral surface of the distal end tip 50 may be covered with the outer coating 60a, which may smooth the outer surface of the distal end tip 50. Thus, the catheter 1 may be capable of easily passing by or through a hard lesion and capable of passing through a tortuous blood vessel, such as a peripheral blood vessel, while preventing and/or reducing the distal end tip 50 from being caught on the patient's anatomy, for example, on a lesion.

The outer covering 60a may be disposed within the slit 52 so that the outer covering 60a is firmly fixed to the distal end tip 50. Such fixing may prevent and/or reduce any separation of the outer coating 60a from the distal end tip 50, for example, separation due to friction with objects outside of the catheter 1. Thus, when the distal end tip 50 passes by or through a calcified lesion, for example, the smooth surface of the distal end tip 50 is securely maintained.

Figure 3:
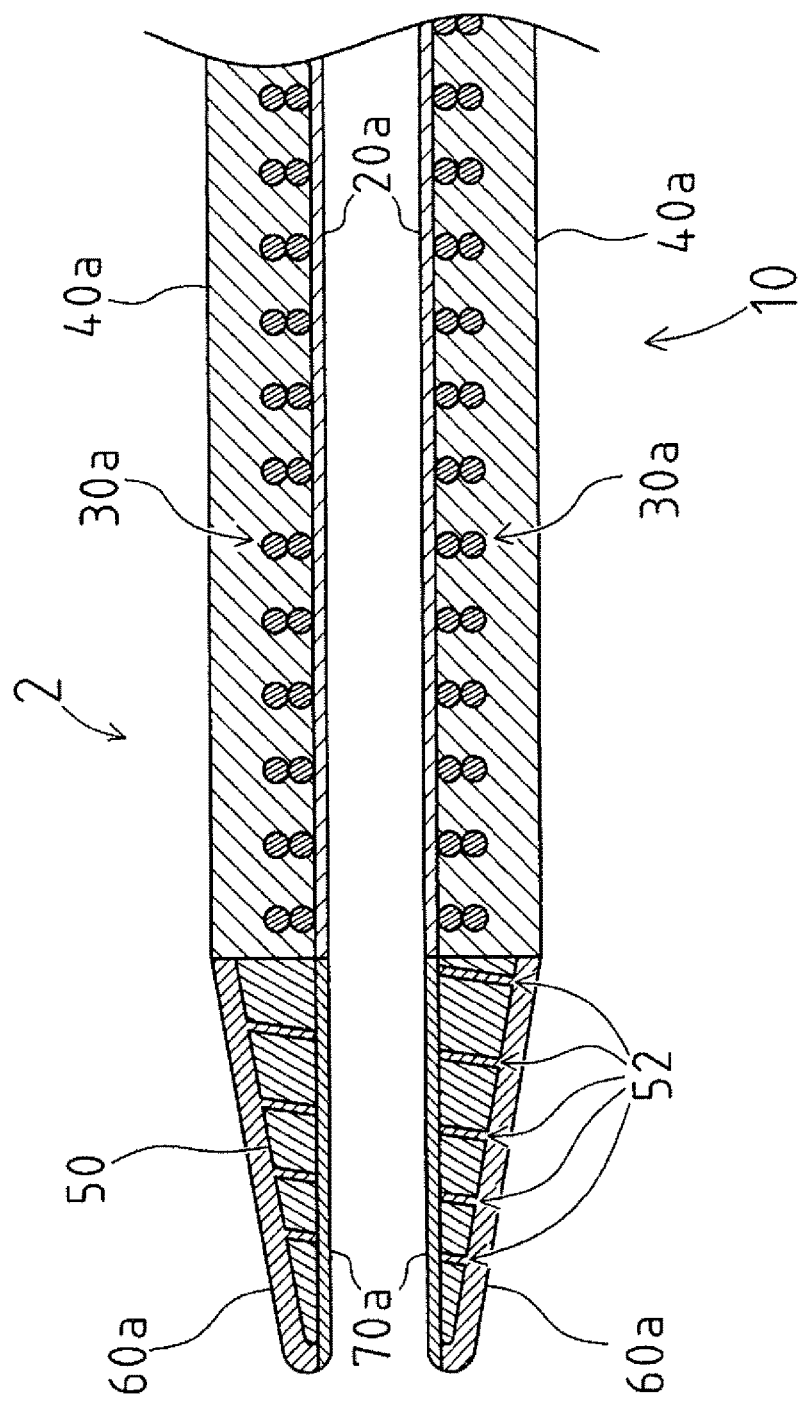
FIG. 3 is another cross-sectional view of part A of a modification of the catheter of FIG. 1.

As shown in FIG. 3, the outer covering 60a may be provided on the outer peripheral surface of the distal end tip 50 and an inner coating 70a may be provided on the inner peripheral surface of the distal end tip 50 of catheter 2. The portion of the outer covering 60a disposed within the slit 52 may contact the inner coating 70a so that the outer coating 60a and the inner coating 70a are in direct contact with each other. Thus, the outer coating 60a and the inner coating 70a may be firmly fixed to the distal end tip 50.

The inner coating 70a may provide a smooth inner peripheral surface to the distal end tip 50, which may prevent a medical instrument (for example, a guide wire) that passes through an inner lumen of the catheter 2 from being caught on the inner peripheral surface of the distal end tip 50.

Figure 4:
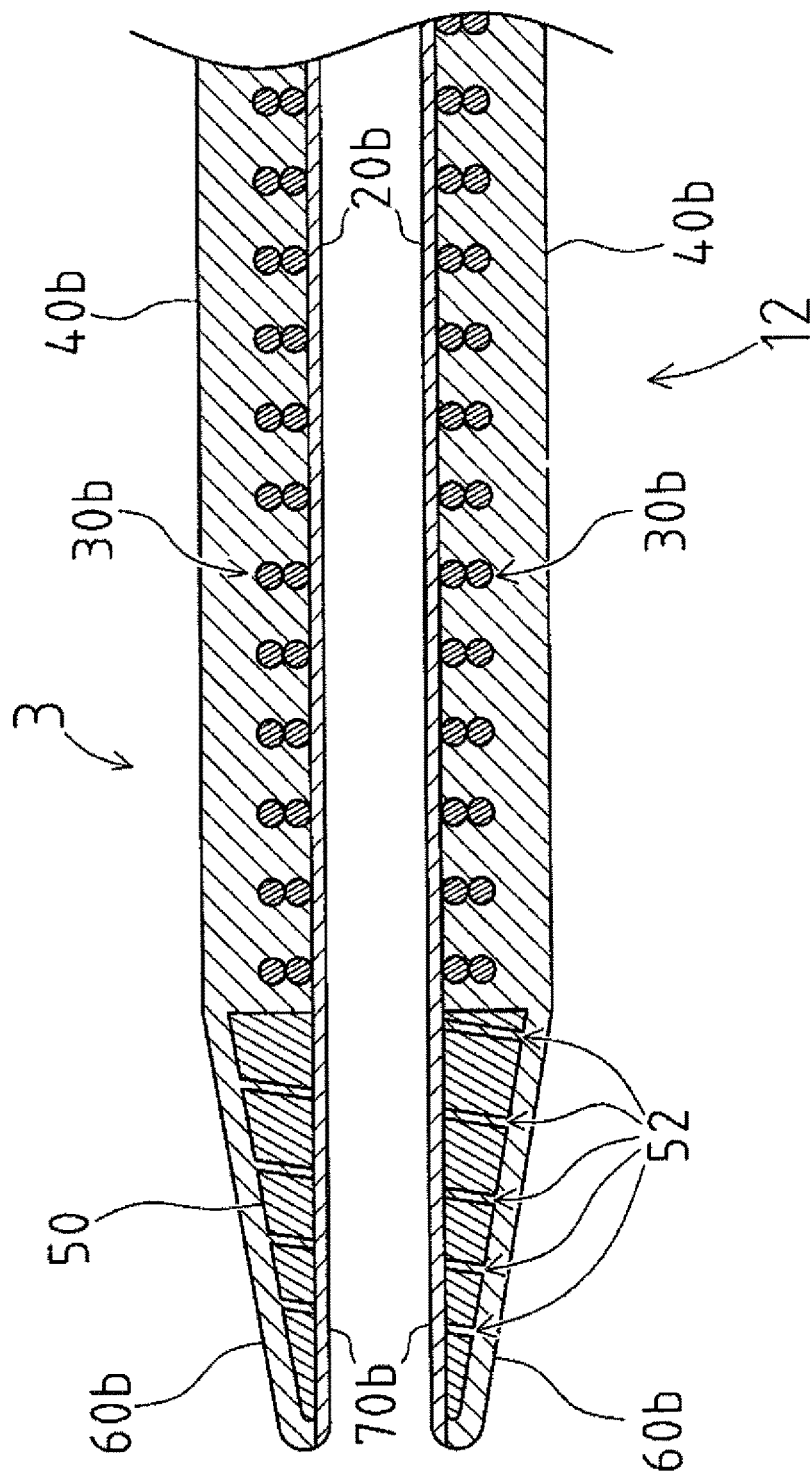
FIG. 4 is another cross-sectional view of part A of a modification of the catheter of FIG. 1.

As shown in FIG. 4, catheter 3 may include a catheter shaft 12 with an inner layer 20b, a braid layer 30b, and an outer layer 40b, similar to the embodiment of FIG. 2. Additionally, the catheter 3 may include an outer coating 60b, inner coating 70b, and slit 52 on distal end tip 50. The outer layer 40b and the outer coating 60b may be integrally formed so that they form one unitary member, and the inner layer 20b and the inner coating 70b may be integrally formed so that they form one unitary member.

Because the outer coating 60b and the outer layer 40b are integrally formed, and because the inner coating 70b and the inner layer 20b are integrally formed, a connection portion between the distal end tip 50 and the catheter shaft 12 may be seamless. Such may prevent the catheter 3 from catching on a patient's anatomy, for example, on a lesion. Additionally, the seamless connection may allow a medical instrument, for example a guide wire, to easily pass through an inner lumen of the catheter 3. The seamless connection may enhance connection strength between the distal end tip 50 and the catheter shaft 12.

Figure 5:
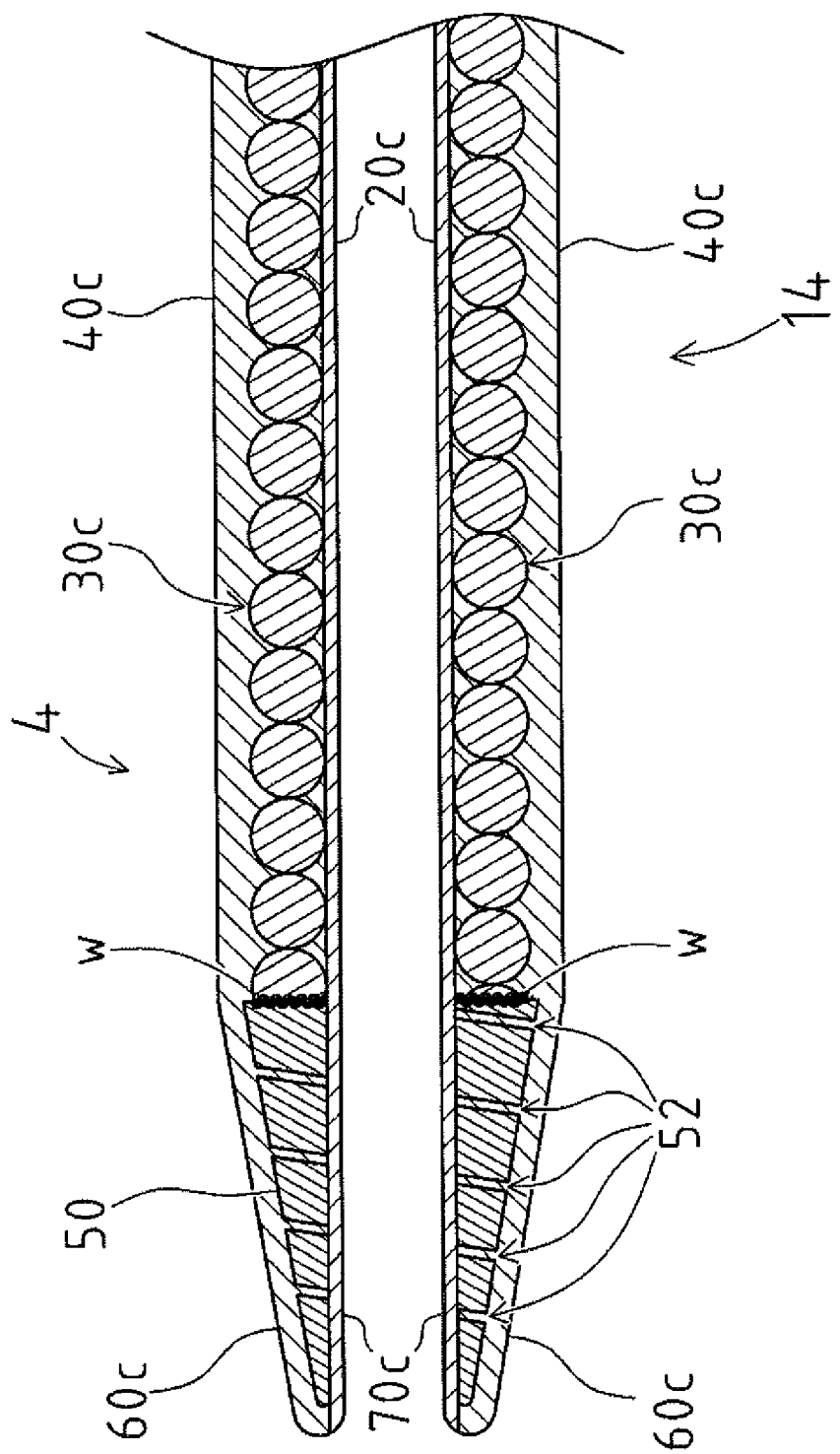
FIG. 5 is another cross-sectional view of part A of a modification of the catheter of FIG. 1.

As shown in FIG. 5, catheter 4 may include a catheter shaft 14 with an inner layer 20c and an outer layer 40c, similar to the embodiment of FIG. 2. Additionally, the catheter 4 may include an outer coating 60c, inner coating 70c, and slit 52 on distal end tip 50. A coil body 30c may be disposed between the inner layer 20c and the outer layer 40c, and the coil body 30c may form a reinforcing body that comprises metallic element wires wound into a helical coil structure. The metallic distal end tip 50 may be welded to the distal end portion of the coil body 30c. As shown in FIG. 5, a welded portion w between the coil body 30c and the distal end tip 50 is illustrated by a bold wave line.

The coil body 30c may be formed by winding a single element wire into a helical coil structure (a single wound coil), or the coil body 30c may be a hollow body formed by winding a plurality of element wires into a helical coil structure (a stranded wire coil). In preferred embodiments, the coil body 30c includes a stranded wire coil in order to sufficiently withstand the rotation force of the catheter 4. The metallic material of the element wires of the coil body 30c is not especially limited, and may include materials known to one of skill in the art, such as, for example, stainless steel (SUS304, SUS316, etc.), gold, white gold, tungsten, platinum, nickel, an alloy of such elements, and mixtures of the materials.

The coil body 30c (the reinforcing body) and the distal end tip 50 may be welded to each other. This may enhance connection strength between the distal end tip 50 and the catheter shaft 14.

Figure 6:
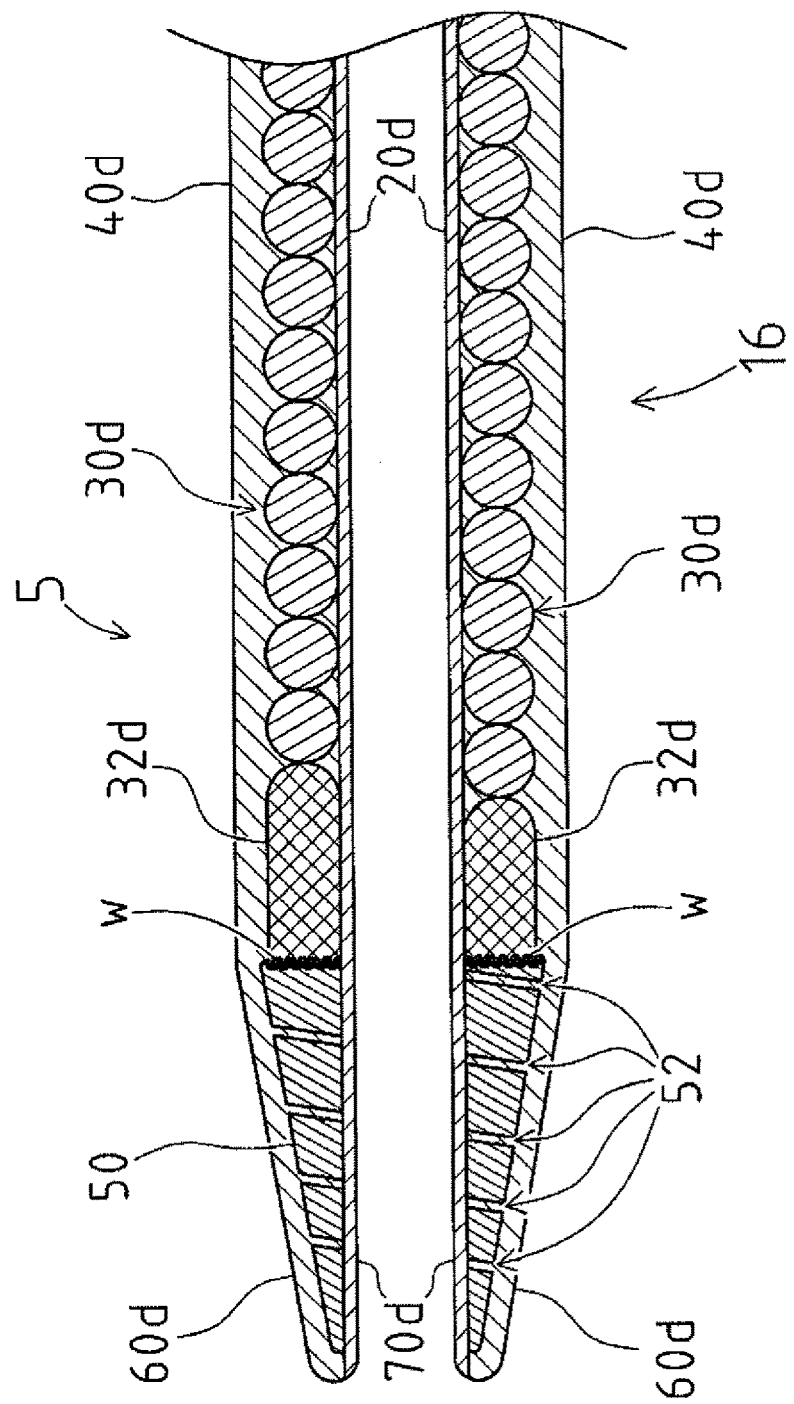
FIG. 6 is another cross-sectional view of part A of a modification of the catheter of FIG. 1.

As shown in FIG. 6, catheter 5 may include a catheter shaft 16 with an inner layer 20d and an outer layer 40d, similar to the embodiment of FIG. 2. Additionally, the catheter 5 may include an outer coating 60d, inner coating 70d, and slit 52 on distal end tip 50. A coil body 30d may be disposed between the inner layer 20d and the outer layer 40d, and the coil body 30d may form a reinforcing body that comprises metallic element wires wound into a helical coil structure. The metallic distal end tip 50 may be welded to the distal end portion 50 of the coil body 30d. As shown in FIG. 6, a welded portion w between the coil body 30d and the distal end tip 50 is illustrated by a bold wave line. Additionally or alternatively, a melted portion 32d may secure the distal end portion 50 to the coil body 30d. The melted portion 32d may by formed integrally with the distal end portion 50 and/or the coil body 30d, and the melted portion 32d may include mutually-melted element wires of the coil body 30d. Thus, the melted portion 32d may weld the distal end portion 50 to the coil body 30d.

The element wires may be mutually and integrally formed with the distal end portion of the coil body 30d to prevent and/or reduce loosening of the element wires from the coil body 30d. As a result, the distal end tip 50 and the distal end portion of the coil body 30d may be easily joined together.

What is claimed is:

1. A catheter comprising:
   a tube body including an inner layer, a reinforcing body covering the inner layer, and an outer layer covering the reinforcing body;
   a tubular metallic distal end tip provided at a distal end of the tube body;
   a slit on the distal end tip; and
   an outer coating on an outer peripheral surface of the distal end tip, at least part of the outer coating is disposed within the slit,
   wherein:
      the distal end tip has a tapered portion so that a diameter of the distal end tip decreases toward a distal end of the distal end tip, and
      a depth of the slit gradually reduces towards the distal end of the distal end tip.

2. The catheter according to claim 1, further comprising an inner coating on an inner peripheral surface of the distal end tip, wherein the outer coating contacts a portion of the inner coating.

3. The catheter according to claim 2, wherein
   the outer coating and the outer layer of the tube body are integrally formed, and
   the inner coating and the inner layer of the tube body are integrally formed.

4. The catheter according to claim 1, wherein
   the reinforcing body is a coil body that includes metallic element wires wound into a helical coil structure, and
   the distal end tip is welded to a distal end of the coil body.

5. The catheter according to claim 4, wherein the distal end of the coil body is connected to the distal end tip with a melted portion.

6. The catheter according to claim 5, wherein the melted portion includes mutually-melted element wires of the coil body.

7. The catheter according to claim 1, wherein the slit is a helical slit.

8. The catheter according to claim 1, wherein the reinforcing body is welded to the distal end tip.

9. The catheter according to claim 4, wherein the reinforcing body is welded to the distal end tip.

10. The catheter according to claim 3, wherein a connection between the distal end tip and the tube body is seamless.

11. A catheter comprising:
    a tube body including an inner layer, a coil body covering the inner layer, and an outer layer covering the coil body;
    a distal end tip provided at a distal end of the tube body;
    a slit on the distal end tip; and
    a first coating on a first peripheral surface of the distal end tip such that the first coating is disposed within the slit,
    wherein:
       the distal end tip has a tapered portion so that a diameter of the distal end tip decreases toward a distal end of the distal end tip, and
       a depth of the slit gradually reduces towards the distal end of the distal end tip.

12. The catheter according to claim 11, wherein the first peripheral surface is an outer peripheral surface of the distal end tip.

13. The catheter according to claim 12, further comprising an inner coating on an inner peripheral surface of the distal end tip, wherein the first coating contacts a portion of the inner coating.

14. The catheter according to claim 11, wherein the slit is a helical slit.

15. The catheter according to claim 11, further comprising second coating on a second peripheral surface of the distal end tip, the second coating contacting a portion of the first coating at a distal end of the distal end tip.

* * * * *